(12) United States Patent
Matsuda et al.

(10) Patent No.: US 7,454,843 B2
(45) Date of Patent: Nov. 25, 2008

(54) MEASURED OBJECT MOUNTING TOOL AND PRODUCTION METHOD OF THREE-DIMENSIONAL SHAPE DATA OF DENTAL PROSTHESIS USING THAT TOOL

(75) Inventors: Yoshinori Matsuda, Itabashi-ku (JP); Yuki Sakamoto, Itabashi-ku (JP); Yoshinori Ebihara, Itabashi-ku (JP)

(73) Assignee: GC Corporation, Tokyo (JP)

( * ) Notice: Subject to any disclaimer, the term of this patent is extended or adjusted under 35 U.S.C. 154(b) by 356 days.

(21) Appl. No.: 11/259,140

(22) Filed: Oct. 27, 2005

(65) Prior Publication Data

US 2006/0093985 A1    May 4, 2006

(30) Foreign Application Priority Data

Oct. 28, 2004    (JP) ............... 2004-314485

(51) Int. Cl.
*G01B 5/004*    (2006.01)
*A61C 19/04*    (2006.01)

(52) U.S. Cl. ................................ 33/503; 33/513

(58) Field of Classification Search ............ 33/503, 33/512, 513, 514; 433/72, 202.1, 197; 600/587; 702/155, 167
See application file for complete search history.

(56) References Cited

U.S. PATENT DOCUMENTS 4,840,564 A * 6/1989 Segal .................. 433/72
5,467,289 A * 11/1995 Abe et al. ................ 702/167
5,758,429 A * 6/1998 Farzan et al. .............. 33/503
5,924,862 A * 7/1999 White .................... 433/72
6,640,150 B1 * 10/2003 Persson et al. ............ 433/213
2006/0037208 A1* 2/2006 McMurtry ................ 33/554
2006/0090361 A1* 5/2006 Matsuda et al. ............ 33/503
2006/0101660 A1* 5/2006 Takanashi .................. 33/503

FOREIGN PATENT DOCUMENTS

| EP | 0 600 800 A1 | 6/1994 |
| JP | 05-332731 | 12/1993 |
| JP | 07-181022 | 7/1995 |
| JP | 2002-257511 | 9/2002 |

* cited by examiner

*Primary Examiner*—G. Bradley Bennett
(74) *Attorney, Agent, or Firm*—Oblon, Spivak, McClelland, Maier & Neustadt, P.C.

(57) ABSTRACT

A measured object mounting tool 2 for producing a three-dimensional shape data comprises a placing part 2b at the lower face of a cylindrical part 2a, an inclined part 2c at a boundary between the side face and the upper face of the cylindrical part 2a, and a pillar part 2d at the upper face of the cylindrical part 2a, where the pillar part 2d has a mounting part 2e at the upper face thereof, a three-dimensional coordinate other than the engaging portion 3a of a model 3 is produced by engaging the model of the dental prosthesis with the mounting part 2e of the tool 2 on a placing table 1; detecting a position where a received light amount is remarkably decreased to by a laser sensor detect a lower end of the inclined part 2c; and thereby calculating an upper end of the engaging portion 3a.

4 Claims, 4 Drawing Sheets

MEASURED OBJECT MOUNTING TOOL AND PRODUCTION METHOD OF THREE-DIMENSIONAL SHAPE DATA OF DENTAL PROSTHESIS USING THAT TOOL

BACKGROUND OF THE INVENTION

1. Field of the Invention

The present invention relates to a measured object mounting tool used for placing a model of a dental prosthesis when three-dimensional coordinates of a shape of the model of the dental prosthesis, which is a measured object, are measured by a three-dimensional measuring device. Further, the present invention relates to a production method of three-dimensional data of a dental prosthesis for cutting a block when cutting the dental prosthesis by an automatic cutting machine using the measured object mounting tool so as to have the same shape as the model of the dental prosthesis, which is the measured object.

2. Description of the Conventional Art

As a general production method of the dental prosthesis such as an inlay, a crown, a bridge or the like, the following methods have been widely known. One method comprises casting of a metallic material by a lost wax casting method, to thereby produce the dental prosthesis. Another method comprises building up a ceramics material on a refractory model, and baking it in a vacuum electric furnace, to thereby produce a dental prosthesis for the purpose of aesthetic appreciation, such as a ceramic inlay, an all ceramic crown or the like.

However, as for the work for producing a dental prosthesis by the conventional method such as the lost wax casting method, the baking by the vacuum electric furnace or the like, almost all processes are carried out by manual labor of a dental technician. Further, the process by the manual labor is remarkably fine and complicated. Thus, such the process takes remarkable time and effort, and the quality of the dental prosthesis, such as accurate or not, is influenced by the level of skill of a dental technician.

Then, as a method for producing a dental prosthesis having the stable quality in a short time in more quantity without depending on manual labor of a dental technician, a dental CAD/CAM system for producing a dental prosthesis has been developed in recent years. In this technique, the dental prosthesis is produced by the steps of producing the three-dimensional shape data of the dental prosthesis such as the inlay, the crown, the bridge or the like using a three-dimensional measuring device, a computer or the like, and cutting the block for cutting of the dental prosthesis by an automatic cutting machine on the basis of the obtained three-dimensional shape data of the dental prosthesis.

As such the three-dimensional measuring device in the dental CAD/CAM system, for example, a device comprising a holding base for a measured object, a rotating jig for the holding base, a changing jig for a holding base rotating shaft, a changing jig for a holding base position, and a laser measuring part, is used (for example, refer to Japanese Patent Application Laid Open No. 5-332731).

Such the device is effective when a model of a small type dental prosthesis applied to only one tooth, such as the inlay, the crown or the like is measured to thereby produce three-dimensional shape data of the dental prosthesis. However, the device has a structure where only the holding base of the measured object is rotated by the rotating jig, so that there is a problem that a large size measured object such as a model of a large-sized type dental prosthesis applied to a plurality of teeth, like a bridge, a gypsum model of a plurality of remaining teeth, or the like, cannot be measured.

Then, for example, the following three-dimensional devices capable of measuring a large size measured object such as a model of a large size dental prosthesis applied to a plurality of teeth, like a bridge, a gypsum model of a plurality of remaining teeth, or the like, to thereby produce the three-dimensional shape data, has been developed. One is a device comprising a body base, a rotary stage, an XY stage, a drive control means, a measured object holding means, an R stage, a first laser displacement gauge, a Z stage, and a second laser displacement gauge (for example, refer to Japanese Paten Application Laid Open No. 7-181022). In this device, the XY stage is movable in a specified horizontal direction X and a horizontal direction Y rectangular to the direction X independently from the rotation of the rotary stage, and has a fitting part for fitting with another member. The drive control means controls the drives of the rotary stage and the XY stage respectively. The measured object holding means has a part to be fitted with a fitting part of the XY stage, and a fitting part for fitting with the measured object. The R stage is movable in the diameter direction of the rotary stage. The first laser displacement gauge is provided at the under face of the R stage so as to have an optical axis parallel to a rotating shaft of the rotary stage. The Z stage is movable in the direction parallel to the rotating shaft. The second laser displacement gauge is provided at the side face of the Z stage so as to be rectangular to the rotating shaft. Further, another is a device comprising Xθ and Yθ stages, a first drive means, X and Y stages, a fixing tool, a second drive means, an optical probe, and a computer (for example, refer to Japanese Patent Application Laid Open No. 2002-257511). In this device, the Xθ and Yθ stages are rotatable in Xθ and Yθ directions. The first drive means finely drives these Xθ and Yθ stages respectively. The X and Y stages move in X and Y directions on the Xθ and Yθ stages. The fixing tool fixes the measured object having the spherical face on the X and Y stages. The second drive means finely drives the X and Y stages respectively. The optical probe measures the three-dimensional coordinate values of the face of the measured object. The computer controls the first drive means and the optical probe, and also makes arithmetic processing of signal.

Those devices can measure a large size measured object, such as a model of the large size dental prosthesis applied to a plurality of teeth, like a bridge, the gypsum model of the plurality of remaining teeth, or the like, and make the three-dimensional shape data. However, the devices are complicated themselves, are difficult to be controlled, and involve high production cost. Especially, as for the former device, since it is provided with two laser displacement gauges, there is a problem that the maintenance and production costs are high.

Then, the three-dimensional measuring device capable of measuring both a small measured object, such as a model of the small type dental prosthesis applied to the one teeth, like an inlay or a crown, and a large measured object, such as a model of a large type dental prosthesis applied to a plurality of teeth, like a bridge, or a gypsum model of a plurality of remaining teeth, or the like, and reducing the production and maintenance costs by having one laser sensor for measuring the shape of the measured object, is developed. That device comprises a rotary table, a XY table, and a measuring part for measuring three-dimensional coordinates of a shape of a measured object. In this device, the rotary table has a rotating shaft, the axis of which is Z axis. The XY table is arranged on the rotary table, movable in an X axial direction and a Y axial direction, and has a placing table fixed on the upper part thereof for a measured object mounting tool being provided thereon. The measuring part measures the three-dimensional coordinates of the measured object shape mounted to the measured object mounting tool on the placing table by one laser sensor, which rotationally moves on one plane containing the Z axis around a desired point on the Z axis and moves in the Z axial direction.

As a method for measuring a model of a dental prosthesis such as an inlay, a crown, a bridge or the like to thereby produce three-dimensional shape data by such the device, for example, the following methods have been carried out. One method comprises, providing a model of a dental prosthesis on the placing table in the three-dimensional measuring device so as to direct its jawbone side, which is to be engaged with an abutment tooth, to the side direction, measuring it, and thereby making the three-dimensional shape data. The model of the dental prosthesis is formed with a wax, a synthetic resin or the like. (Hereinafter, this method is referred to as "a former production method of three-dimensional shape data".) Another method comprises, providing a model of a dental prosthesis in the state of being engaged with a model of an abutment tooth or a model of a residual ridge on the placing table in the three-dimensional measuring device, measuring it, removing the model of the dental prosthesis, measuring parts where the model of the dental prosthesis has been contacted in the model of the abutment tooth or the model of the residual ridge, and thereby producing the three-dimensional shape data of the model of the dental prosthesis on the basis of the respective measured values. The model of the dental prosthesis is formed with a wax, a synthetic resin or the like. (Hereinafter, this method is referred to as "a latter production method of three-dimensional shape data".)

The above respective production methods of the three-dimensional shape data can be sufficiently used, when making three-dimensional shape data of a dental prosthesis by measuring a model of the dental prosthesis such as an inlay, a crown, a bridge or the like, which does not need comparatively high measuring accuracy and processing accuracy, to thereby make the dental prosthesis by cutting a block for cutting of the dental prosthesis by an automatic cutting machine on the basis of the produced three-dimensional data of the dental prosthesis. However, when making a dental prosthesis for an implant applied for only one implant fixture, for example, which requires remarkably high measuring and processing accuracies, even both of above production methods of three-dimensional shape data have a problem that it is quite difficult to produce the dental prostheses having the necessary dimensional accuracy.

As the dental prosthesis for an implant applied to only one implant fixture, for example, there is a dental prosthesis in which an artificial tooth and an engaging portion are formed to have an integral shape, and provided and fixed at an intraoral side part of the implant fixture embedded into the jawbone, directly or through the conventional abutment. In addition, there is an abutment or the like, in which a part contacted with gingiva and a part fixed with an artificial tooth are designed corresponding to the shapes of the gingiva and adjacent teeth of a patient, who is applied with the dental prosthesis, and in which an engaging portion for engaging with the implant fixture embedded into the jawbone is provided. In such the engaging portion projected toward the jawbone side of the dental prosthesis for an implant, a projected and/or recessed engaging part is formed to have a sectional shape other than that of rotating body (regular hexagon in general). Thus, when three-dimensional shape data of a model of a dental prosthesis for the implant is produced by the above described former production method of three-dimensional shape data, there is a problem that the engaging portion cannot be accurately measured, since laser light of a laser sensor of a measuring part can not reach to the inner part of the engaging portion, and the placing table or the XY tables becomes an obstacle when measuring a part on the placing table side of the engaging part. On the other hand, when three-dimensional shape data of a model of a dental prosthesis for an implant is produced by the above described latter production method of three-dimensional shape data, it is necessary to prepare a model of the dental prosthesis for the implant and a model of a implant fixture or an abutment engaged with this model of the dental prosthesis for the implant and measure the portion contacted with the engaging portion of the model of the dental prosthesis in the implant fixture or the abutment. Thus, there is a problem that the time and labour are necessary for preparing the model of the implant fixture or the abutment. Further, when the portion contacted with the engaging portion of the model of the dental prosthesis in the implant fixture or the abutment is measured, there is a problem that the engaging portion cannot be accurately measured, since laser light of the laser sensor of the measuring part can not reach to the inner part of the engaging portion, like the case of the former production method of three dimensional shape data.

Further, the engaging portion of the dental prosthesis for the implant has a polygonal shape having corner parts, for example, regular hexagon in general, so that there is a problem that it is difficult to accurately measure this engaging portion by a laser sensor of a general three-dimensional measuring device. Further, if the produced three-dimensional shape data of the engaging portion of the dental prosthesis is even slightly differed from the actual shape of the engaging portion of the model of the dental prosthesis, there may be a problem that the dental prosthesis cannot be engaged well with the implant fixture, or is loosened after fixing with the implant fixture when the dental prosthesis is fixed with the implant fixture, as the dental prosthesis is made by cutting a block for the dental prosthesis by the automatic cutting machine on the basis of the inaccurate three-dimensional data of the dental prosthesis.

Further, even when the former or latter production method of three-dimensional shape data can obtain accurate three-dimensional shape data of the model of the dental prosthesis, there is a problem that the dental prosthesis according to the produced three-dimensional shape data cannot be accurately produced when the engaging portion has the shape having the corner parts, since the automatic cutting machine, which makes a dental prosthesis on the basis of three-dimensional shape data of a model of a dental prosthesis, cuts the block by using a rotationally cutting tool in general.

SUMMARY OF THE INVENTION

The present invention solves the above-mentioned problems of the conventional techniques, and the primary objective of the present invention is to provide a measured object mounting tool used for providing a model of a dental prosthesis, when three-dimensional coordinates of a shape of the model of the dental prosthesis, which is a measured object, is measured by a three-dimensional measuring device. In this measured object, an engaging portion having a projected and/or recessed engaging part is projected, at a jawbone side where the engaging part has a cross sectional shape other than that of a rotary body. This three-dimensional measuring device comprises a rotary table, an XY table, and a measuring part for measuring three-dimensional coordinates of a shape of the measured object. In this device, the rotary table has the rotating shaft, the axis of which is Z axis. The XY table has a placing table fixed on the upper part of the XY table for a measured object mounting tool being provided thereon, is movable in an X axial direction and a Y axial direction, and is arranged on the rotary table. The measuring part measures the three-dimensional coordinates of the measured object, which is mounted on the measured object mounting tool on the placing table, by using one laser sensor, which rotationally moves on one plane containing the Z axis around a desired point on the Z axis, and moves in the Z axial direction. Further, another objective of the present invention is to provide the production method of three-dimensional shape data of a dental prosthesis, where the data is for cutting a block for cutting the dental prosthesis to the same shape as the measured object using the measured object mounting tool by an automatic cutting machine.

The earnest work was carried out in order to solve the above-mentioned problems and, as a result of this, the followings were found. When a block for cutting a dental prosthesis is cut by an automatic cutting machine to thereby produce a dental prosthesis, on the basis of three-dimensional shape data of a model of the dental prosthesis obtained by using the three-dimensional measuring device, an engaging portion, which has the projected and/or recessed engaging part on the jawbone side having the cross sectional shape other than that of the rotary body, and a portion other than the engaging portion are not machined simultaneously, but only the portion other than the engaging portion is cut by the automatic cutting machine, using a block for cutting a dental prosthesis where a engaging portion having the approximately same shape as the engaging portion of the model of the dental prosthesis is preformed. Then, the above-mentioned problems of the measuring accuracy of the three-dimensional measuring device and the processing accuracy of the automatic cutting machine, or the like can be solved.

However, the following problem was found. When the model of the dental prosthesis is measured in the state, where the model is mounted on the measured object mounting tool on the placing table, by the three-dimensional measuring device, the three-dimensional shape data of only the portion other than the engaging portion of the model of the dental prosthesis can not be obtained but the three-dimensional shape data in the state where the model of the dental prosthesis and the measured object mounting tool are integrated and the boundary of those can not be distinguished, is obtained, while the three-dimensional shape data of only the portion other than the engaging portion of the model of the dental prosthesis is necessary for cutting the block for cutting of the dental prosthesis by the automatic cutting machine, where the approximately same shape as the engaging portion of the model of the dental prosthesis is preformed on the block. When the block for cutting of the dental prosthesis is cut on the basis of such the three-dimensional shape data in the state where the boundary of each part cannot be distinguished, it is necessary to do the very hard work to extract the three-dimensional data of only the portion other than the engaging portion of the model of the dental prosthesis.

Further, in a case of extracting the three-dimensional shape data of only the portion other than the engaging portion of the model of the dental prosthesis, since a position of an upper end of the engaging portion, which is the boundary of the engaging portion and the portion other than the engaging portion of the model of the dental prosthesis, cannot be accurately distinguished, if the three-dimensional shape data of a part, which is upper than the position of the upper end of the engaging portion, is extracted with slightly mistaking this position, the dental prosthesis having the same shape as that of the model of the dental prosthesis cannot be made. Thus, when the produced dental prosthesis is actually mounted, there are problems that the dental prosthesis interferes to an adjacent tooth, the position of an occlusal face cannot be the right position, and the dental prosthesis cannot be mounted well with the implant fixture. Further, more particularly, when the produced dental prosthesis is the above-mentioned abutment, there is a problem that aesthetic appreciation is remarkably damaged since the abutment is not fitted to a shape of a gingiva of a patient, the abutment itself is seen from the upper side of the gingiva, or the abutment is embedded into the gingiva.

From these reasons, the present inventors found out the following new method as a method for extracting the three-dimensional shape data of only the portion other than the engaging portion of the model of the dental prosthesis from the three-dimensional shape data, where the model of the dental prosthesis and the measured object mounting tool are integrated and the boundary of each part cannot be distinguished. The new method comprises the steps of recognizing the boundary of a cylindrical part of the measured object mounting tool provided with the model of the dental prosthesis and a pillar part perpendicularly erected at the upper face of the cylindrical part and provided with the model of the dental prosthesis at the upper face thereof from the three-dimensional shape data, calculating the position of the upper end of the engaging portion of the model of the dental prosthesis on the basis of the distance pre-memorized between the positions of the boundary of the measured object mounting tool and the upper end of the engaging portion of the model of the dental prosthesis in the state where the model of the dental prosthesis is mounted, and thereby extracting the three-dimensional shape data of only the portion other than the engaging portion of the model of the dental prosthesis. However, the laser light is irregularly reflected on the portion bent at an approximately right angle like the boundary, from the reason of the characteristic of the laser sensor of the general three-dimensional measuring device. Thus, the position of the boundary on the three-dimensional shape data is inaccurate, so that the boundary of the cylindrical part and the pillar part in the measured object mounting tool can not be recognized accurately by such the method.

Then, the further earnest work is carried out to solve the above problem of detecting the position of the upper end of the engaging portion from the three-dimensional shape data, when the model of the dental prosthesis and the measured object mounting tool are integrated and the boundary of each part cannot be distinguished. As a result of this, the followings were found out to complete the present invention. In this invention, instead of detecting such the position of the upper end of the engaging portion, the position of the lower end of an inclined part of the measured object mounting tool can be accurately detected by the steps of using a measured object mounting tool having the inclined part formed by a part of a conical shape at the boundary of the side face and the upper face of the cylindrical part, where the conical shape has an angle of 20 to 70 degrees with respect to a center axis of the cylindrical part, irradiating the laser light from the side face of the cylindrical part to the inclined part of the measured object mounting tool while keeping the state where the laser light is irradiated in parallel with the upper face of the cylindrical part, measuring a light receiving amount of the laser light, and defecting the position where the light receiving amount is remarkably decreased. Then, the three-dimensional coordinates of the portion other than the engaging portion of the model of the dental prosthesis can be accurately produced on the basis of the position of the lower end of the inclined part of the measured object mounting tool.

Thus, one aspect of the present invention is a measured object mounting tool used for providing a model of a dental prosthesis when three-dimensional coordinates of a shape of a measured object, the model of the dental prosthesis with an engaging portion projected on the jawbone side having a projected and/or recessed engaging part, being and the having a cross sectional shape other than that of the rotary body, is measured by a three-dimensional measuring device comprising the rotary table having a rotating shaft, the axis of which is Z axis, the XY table which has a placing table for providing the measured object mounting tool fixedly on the upper part thereof, is movable in an X axial direction and Y axial direction, and arranged on the rotary table, and a measuring part for measuring the three-dimensional coordinates of the shape of the measured object mounted on the measured object mounting tool on the placing table by one laser sensor, which rotationally moves on one plane containing the Z axis around a desired point on the Z axis, and moves in a Z axial direction, wherein this measured object mounting tool comprises the cylindrical part, the placing part, the inclined part, the pillar part, and the mounting part, the placing part is provided at the lower face side of the cylindrical part and formed so as to perpendicularly place the center axis of the cylindrical part with respect to an upper face of the XY table on the placing table on the XY table, the inclined part is formed by a part of the conical shape having the angle of 20 to 70 degrees with respect to a center axis of the cylindrical part at a boundary part between a side face and an upper face of the cylindrical part, the pillar part is perpendicularly erected on the upper face side of the cylindrical part, formed to have a same cross sectional shape as a cross sectional shape of an engaging portion of the model of the dental prosthesis, and formed so as to position an extension line of the center axis of the cylindrical part in the engaging portion, and the mounting part is formed on an upper face of the pillar part and has a shape for engaging with the engaging part of the engaging portion of the model of the dental prosthesis.

Further, the one aspect of a production method of three-dimensional shape data of the dental prosthesis using the measured object mounting tool according to the present invention is a production method of three-dimensional data for cutting a block for cutting the dental prosthesis by an automatic cutting machine to have the same shape as that of the measured object, by using the three-dimensional measuring device comprising the rotary table having the rotating shaft, the axis of which is the Z axis, the XY table which has the placing table for providing the measured object mounting tool fixedly on the upper part thereof, is movable in the X axial direction and the Y axial direction, and arranged on the rotary table, and the measuring part for measuring the three-dimensional coordinates of the shape of the measured object mounted on the measured object mounting tool on the placing table by one laser sensor, which rotationally moves on one plane containing the Z axis around a desired point on the Z axis, and moves in the Z axial direction, Wherein this method comprises steps of:

a model preparing step for preparing the model of the dental prosthesis as the measured object, where the model of the dental prosthesis has the engaging portion projected on the jawbone side and the engaging portion has the projected and/or recessed engaging part having the cross sectional shape other than that of a rotary body and a model providing step for preparing the measured object mounting tool according to the present invention and engaging the engaging part of the engaging position of the model of the dental prosthesis with a mounting part of the measured object mounting tool, a mounting tool placing step for placing the measured object mounting tool with the model of the dental prosthesis on the placing table, a model mounted tool measuring step for rotating the rotary table around the Z axis as the axis thereof, keeping the laser light irradiated from the laser sensor to be in parallel with upper face of the cylindrical part of the measured object mounting tool, moving the laser sensor in the Z axial direction by the measuring part so as to transfer an irradiated portion by laser light to the position of the height before reaching to the top of the pillar part of the measured object mounting tool from the side face of the cylindrical part of the measured object mounting tool passing through the inclined part of the measured object mounting tool and then rotationally moving the laser sensor to thereby measure the received light amount of the laser light from the cylindrical part and the pillar part of the measured object mounting tool and the model of the dental prosthesis, and the three-dimensional coordinates of the shapes thereof, and a three-dimensional coordinate extracting step for detecting the position where the received light amount of the laser light is remarkably decreased when transferring from the side face of the cylindrical part of the measured object mounting tool to the inclined part, detecting the coordinate on the Z axis of the position of the lower end of the inclined part of the measured object mounting tool, calculating the coordinate on the Z axis of the position of the upper end of the engaging portion of the model of the dental prosthesis on the basis of the prememorized distance on the Z axis between the positions of the lower end of the inclined part of the measured object mounting tool and the upper end of the engaging portion of the model of the dental prosthesis, where the model of the dental prosthesis is provided on the measured object mounting tool, and extracting only the three-dimensional coordinates of the shape other than the engaging portion of the model of the dental prosthesis positioned on the upper side of the coordinate calculated from the measured three-dimensional coordinates, so that the three-dimensional shape data of the dental prosthesis for cutting the block for cutting the dental prosthesis by the automatic cutting machine, where the engaging portion having the approximately same shape as the engaging portion of the model of the dental prosthesis is preformed, can be produced by carrying out these steps in order.

Further, another aspect of a production method of three-dimensional shape data of the dental prosthesis using the measured object mounting tool according to the present invention is a production method of three-dimensional shape data for cutting a block for cutting a dental prosthesis by an automatic cutting machine to have the same shape as that of the measured object, by using the three-dimensional measuring device comprising the rotary table having the rotating shaft, the axis of which is the Z axis, the XY tables, which has the placing table for providing the measured object mounting tool fixedly on the upper part thereof, is movable in the X axial direction and the Y axial direction and arranged on the rotary table, and the measuring part for measuring the three-dimensional coordinates of the shape of the measured object mounted on the measured object mounting tool on the placing table by one laser sensor, which rotationally moves on one plane containing the Z axis around a the desired point on the Z axis, and moves in the Z axial direction.

Wherein this method comprises the steps of:

a model preparing step for preparing the model of the dental prosthesis as the measured object, where the model of the dental prosthesis has the engaging portion projected on the jawbone side and the engaging portion has the projected and/or recessed engaging part having the cross sectional shape other than that of a rotary body, a model providing step for preparing the measured object mounting tool according to the present invention and engaging the engaging part of the engaging potion of the model of the dental prosthesis with the mounting part of the measured object mounting tool, a mounting tool placing step for placing the measured object mounting tool with the model of the dental prosthesis on the placing table, a measuring initial position moving step of keeping the laser light irradiated from the laser sensor to be in parallel to the upper face of the cylindrical part, moving the laser sensor along the Z axis direction by the measuring part so as to transfer the irradiated portion from the side face to the inclined part of the measured object mounting tool, detecting the position where the received light amount of the laser light is remarkably decreased, detecting the coordinate on the Z axis of the position of the lower end of the inclined part of the measured object mounting tool, calculating the coordinate on the Z axis of the position of the upper part of the engaging portion of the model of the dental prosthesis, on the basis of the prememorized distance on the Z axis between the positions of the lower end of the inclined part of the measured object mounting tool and the position of the upper end of the engaging portion of the model of the dental prosthesis, where the model of the dental prosthesis is provided on the measured object mounting tool, and moving quickly the laser sensor by the measuring part to the calculated position of the coordinate in the Z axis direction, and a model mounted tool measuring step of rotating and moving the laser sensor, while rotating the rotary table around the Z axis, and measuring the three dimensional coordinates of the shape of the model of the dental prosthesis other than the engaging portion, so that the three-dimensional shape data of the dental prosthesis for cutting the block for cutting the dental prosthesis by the automatic cutting machine, where the engaging portion having the approximately same shape as the engaging portion of the model of the dental prosthesis is preformed, can be produced by carrying out these steps in order.

Further, in these production steps of the three-dimensional shape data of the dental prosthesis, it was found that when the center axis of the cylindrical part of the measured object mounting tool is not agreed beforehand with the Z axis, these axes can be easily adjusted by carrying out a both axes adjusting step for moving the XY table in the X and/or the Y axis directions in order to agree the center axis of the cylindrical part of the measured object mounting tool with the Z axis, after carrying out the mounting tool placing step. Thus, it is preferable.

Since the measured object mounting tool and the production method of the three-dimensional shape data of the dental prosthesis by using this tool according to the present invention, have the above-mentioned constitutions, these are suitable for producing the three-dimensional shape data of the dental prosthesis, where the engaging portion having the projected and/or recessed engaging part is projected on the jawbone side and has the cross sectional shape other than the rotary body. Further, the present invention has the constitution for measuring the measured object mounting tool having the model of the dental prosthesis, where the tool is placed on the placing table of the present three-dimensional measuring device. Thus, the method can be carried out only by preparing the measured object mounting tool corresponding to the model of the dental prosthesis without big modification or processing to the existing three-dimensional measuring device. As a result of this, the present invention can be applied for measuring not only the measured object of the dental prosthesis, where the engaging portion having the projected and/or recessed engaging part is projected on the jawbone side and has the cross sectional shape other than the rotary body, but also the following various measured objects without purchasing a new three-dimensional measuring device, to thereby be able to the three-dimensional shape data. The present invention can be applied for measuring the small measured object such as the model of the small type dental prosthesis applied to a small number of teeth such as the inlay, the crown or the like, and the large measured object such as the model of the large type dental prosthesis applied to a large number of teeth such as the bridge or the like, or the gypsum model of a large number of remaining teeth.

Further, since the production method of the three-dimensional shape data of the dental prosthesis by using the measured object mounting tool according to the present invention comprises the following steps, the three-dimensional shape data of the dental prosthesis can be made in short time, when the length in the Z axis direction of the measured object mounting tool is comparatively short. The method comprises steps of a model mounted tool measuring step for rotating the rotary table around the Z axis as the axis thereof, keeping the laser light irradiated from the laser sensor to be in parallel with the upper face of the cylindrical part of the measured object mounting tool, moving the laser sensor by the measuring part in the Z axial direction so as to transfer the irradiated portion by laser light to the position of the height before reaching to the top of the pillar part of the measured object mounting tool from the side face of the cylindrical part of this tool passing through the inclined part of this tool, and rotationally moving the laser sensor for measuring the received light amount of the laser light from the cylindrical part and the pillar part of the measured object mounting tool and the model of the dental prosthesis, and the three-dimensional coordinate of these shapes, and a three-dimensional coordinate extracting step for detecting the position where the received light amount of the laser light is remarkably decreased when transferring from the side face to the inclined part of the cylindrical part of the measured object mounting tool, detecting the coordinate on the Z axis of the position of the lower end of the inclined part of the measured object mounting tool, calculating the coordinate on the Z axis of the position of the upper end of the engaging portion of the model of the dental prosthesis on the basis of the prememorized distance on the Z axis between the positions of the lower end of the inclined part of the measured object mounting tool and the upper end of the engaging portion of the model of the dental prosthesis, where the model of the dental prosthesis is provided on the measured object mounting tool, and extracting only the three-dimensional coordinates of the shape exclusive of the engaging portion of the model of the dental prosthesis positioned on the upper side from the coordinate calculated from the measured three-dimensional coordinate. Then, this method has the constitution of measuring at a stretch the received light amounts from the measured object mounting tool and the model of the dental prosthesis, and the three-dimensional coordinates of these shapes, and thereafter, detecting only the three-dimensional coordinates of the shape other than the engaging part of the model of the dental prosthesis. Thus, the method is preferable for making the three-dimensional shape data of the dental prosthesis in short time, when the length in the Z axis direction of the measured object mounting tool is comparatively short.

Further, since the production method of the three-dimensional shape data of the dental prosthesis by using the measured object mounting tool according to the present invention comprises the following steps, the three-dimensional shape data of the dental prosthesis can be made in short time, when the length in the Z axis direction of the measured object mounting tool is comparatively long. The method comprises the steps of a measuring initial position moving step of keeping the laser light parallel to the upper face of the cylindrical part, moving the laser sensor in the Z axis direction by the measuring part so as to transfer the irradiated portion by the laser light from the side face to the inclined part of the measured object mounting tool, detecting the point, where the received light amount of the reflected laser light is extremely decreased, to thereby detect the coordinate on the Z axis of the lower end of the inclined part of the measured object mounting tool, calculating the coordinate on the Z axis of the position of the upper end of the engaging portion of the model of the dental prosthesis, on the basis of the prememorized distance on the Z axis between the positions of the lower end of the inclined part of the measured object mounting tool and the upper end of the engaging portion of the model of the dental prosthesis, where the model of the dental prosthesis is provided on the measured object mounting tool, and moving quickly the laser sensor by the measuring part in the Z axis direction to the calculated position of the coordinate, and a model mounted tool measuring step of rotating and transferring the laser sensor while rotating the rotary table around the Z axis, measuring the three dimensional coordinates of the shape of the model of the dental prosthesis exclusive of its engaging portion. Then, the method has the constitution of measuring only the received light amount of the laser light of the measured object mounting tool, moving at a stretch the laser light to the upper end position of the engaging portion of the model of the dental prosthesis, that is, the initial measuring position, measuring only the three-dimensional coordinates of the shape other than the engaging portion of the model of the dental prosthesis. Thus, the method is preferable for making the three-dimensional shape data of the dental prosthesis in short time, when the length in the Z axis direction of the measured object mounting tool is comparatively long.

Further, in these production methods of the three-dimensional shape data of the dental prosthesis, when the center axis of the cylindrical part of the measured object mounting tool is not agreed beforehand with the Z axis, these axes can be easily adjusted by carrying out a both axes adjusting step for transferring the XY table in the X and/or the Y axis directions in order to agree the center axis of the cylindrical part of the measured object mounting tool to the Z axis, after carrying out the mounting tool placing step, whereby the measuring of the three-dimensional coordinates by the laser sensor of the measuring part, which is done in each step after this step, can be smoothly carried out, and the three-dimensional coordinates of the model of the dental prosthesis on the basis of the Z axis can be obtained. Thus the above step is preferable.

DETAILED DESCRIPTION OF PREFERRED EMBODIMENT

Hereinafter, the production method of the three-dimensional shape data of the dental prosthesis according to the present invention is concretely explained with drawings.

Figure 1:
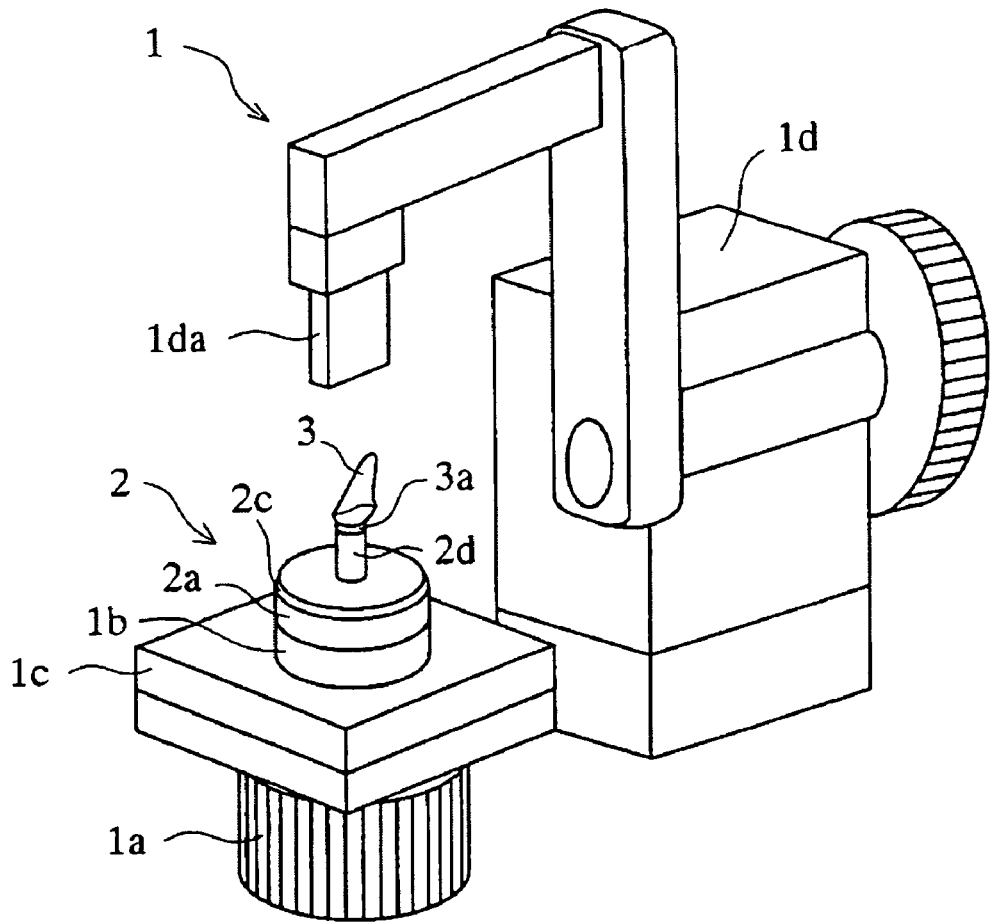
FIG. 1 is a perspective explanation view schematically illustrating one example of a three-dimensional measuring device used in the present invention.
Figure 2:
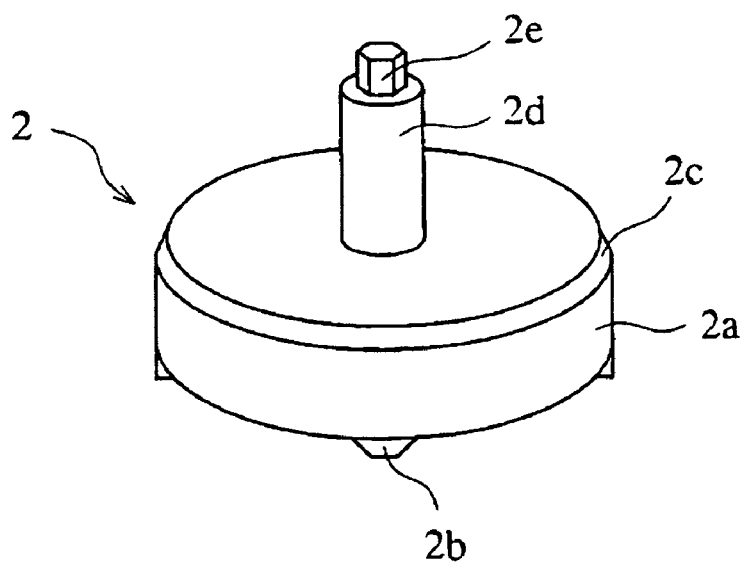
FIG. 2 is a perspective enlarged explanation view illustrating a shape of an upper part of a measured object mounting tool removed from the placing table of the three-dimensional measuring device illustrated in FIG. 1.
Figure 3:
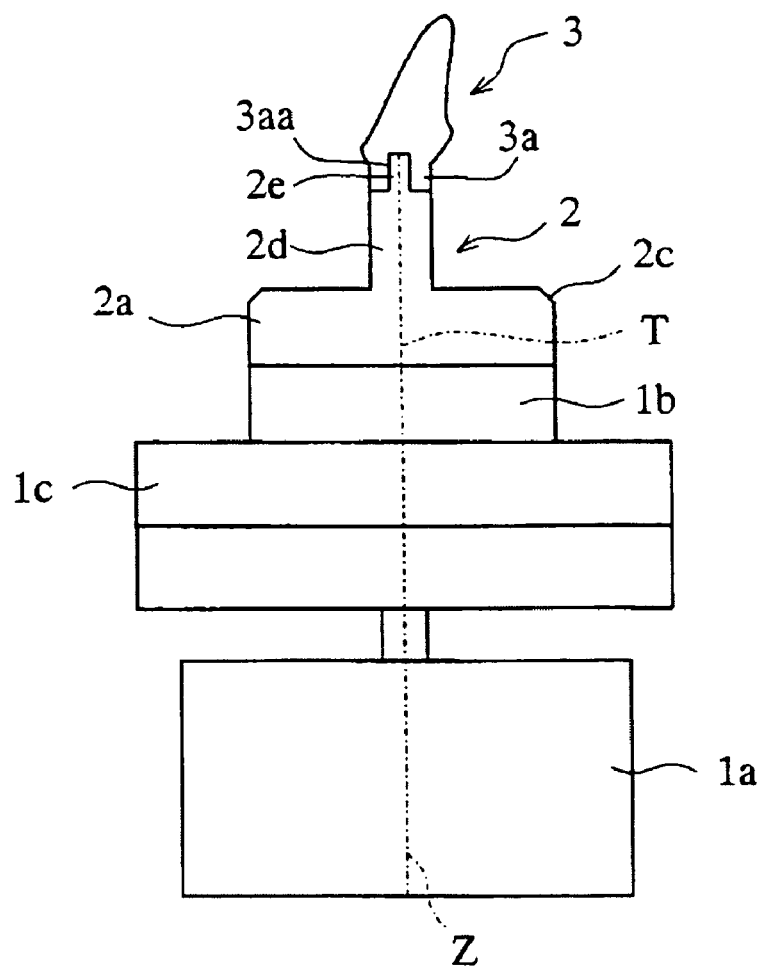
FIG. 3 is a sectional explanation view schematically illustrating the state where the center axis of the cylindrical part of the measured object mounting tool is agreed with the Z axis.
Figure 4:
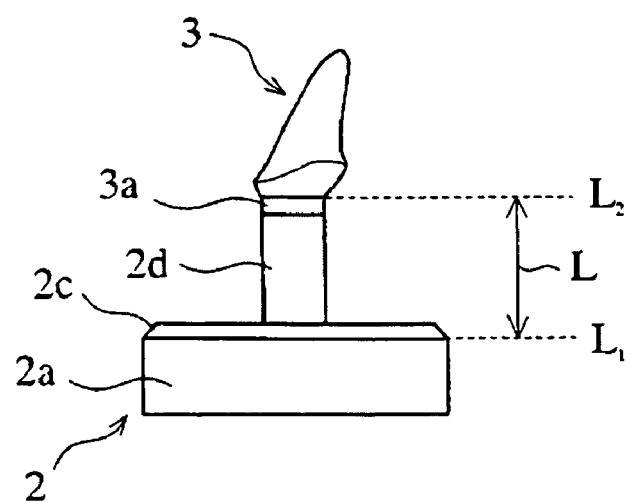
FIG. 4 is a front explanation view schematically illustrating a positional relationship between a lower end position of an inclined part of the measured object mounting tool and an upper end position of an engaging portion of a model of a dental prosthesis in the state that an abutment, which is a model of dental prosthesis, is mounted on the measured object mounting tool.
Figure 5:
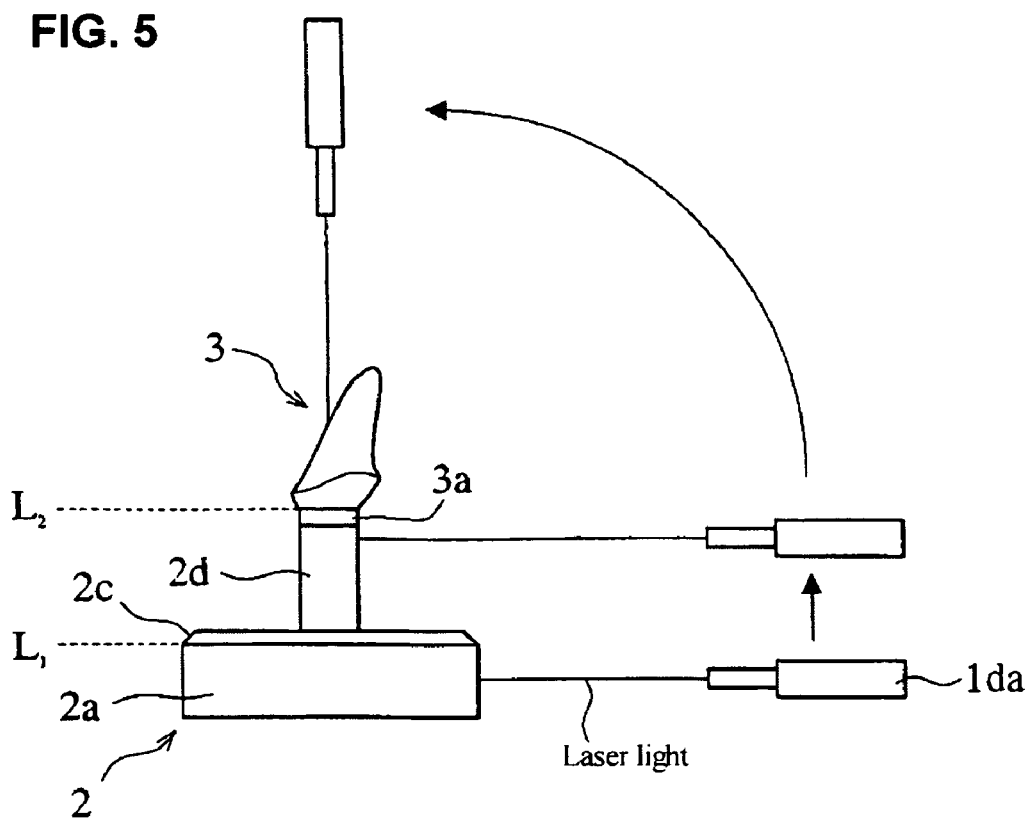
FIG. 5 is a front explanation view schematically illustrating one example of the movement of a laser sensor moved by the measuring part.
Figure 6:
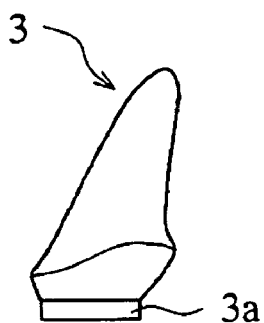
FIG. 6 is a front explanation view schematically illustrating one example of an abutment, which is a model of dental prosthesis used in the present invention.
Figure 7:
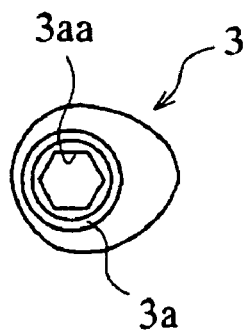
FIG. 7 is an explanation view of a bottom face of FIG. 6.
Figure 8:
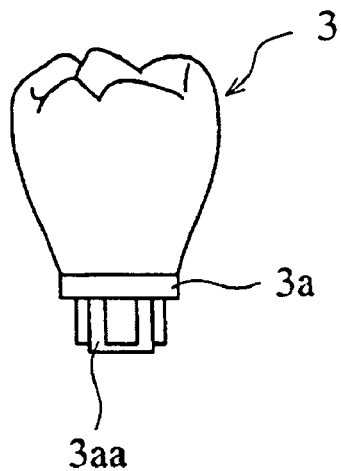
FIG. 8 is a front explanation view schematically illustrating one example of a dental prosthesis having an artificial tooth, which is a model of dental prosthesis used in the present invention.
Figure 9:
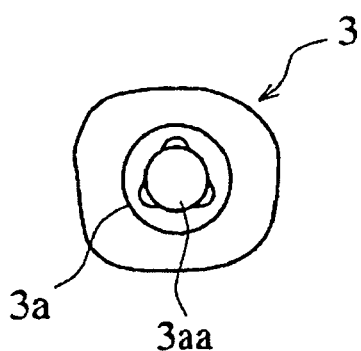
FIG. 9 is an explanation view of a bottom face of FIG. 8.
Figure 10:
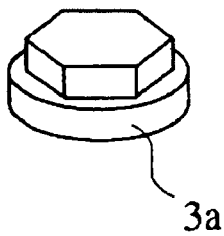
FIG. 10 is a perspective explanation view illustrating one example of a jig having the same shape as that of the engaging portion, which is used when forming a model of the dental prosthesis.
Figure 11:
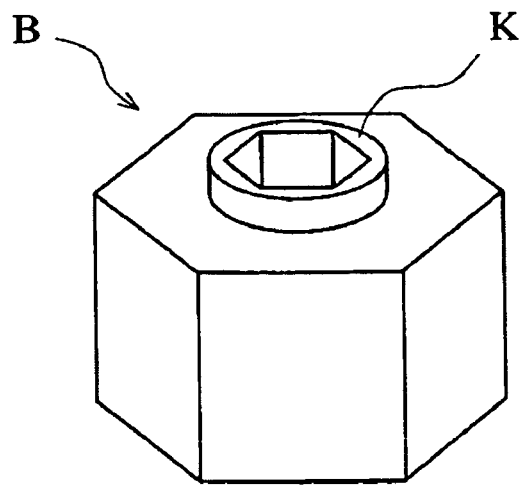
FIG. 11 is a perspective explanation view illustrating one example of a block for cutting the dental prosthesis, which is cut on the basis of a three-dimensional shape data of the dental prosthesis produced by the present invention.

FIG. 1 is a perspective explanation view schematically illustrating one example of a three-dimensional measuring device used in the present invention. FIG. 2 is a perspective enlarged explanation view illustrating a shape of an upper part of a measured object mounting tool removed from the placing table of the three-dimensional measuring device illustrated in FIG. 1. FIG. 3 is a sectional explanation view schematically illustrating the state where the center axis of the cylindrical part of the measured object mounting tool is agreed with the Z axis. FIG. 4 is a front explanation view schematically illustrating a positional relationship between a lower end position of an inclined part of the measured object mounting tool and an upper end position of an engaging portion of a model of a dental prosthesis in the state that an abutment, which is a model of dental prosthesis, is mounted on the measured object mounting tool. FIG. 5 is a front explanation view schematically illustrating one example of the movement of a laser sensor moved by a measuring part. FIG. 6 is a front explanation view schematically illustrating one example of an abutment, which is a model of dental prosthesis used in the present invention. FIG. 7 is an explanation view of a bottom face of FIG. 6. FIG. 8 is a front explanation view schematically illustrating one example of a dental prosthesis having an artificial tooth, which is a model of dental prosthesis used in the present invention. FIG. 9 is an explanation view of a bottom face of FIG. 8. FIG. 10 is a perspective explanation view illustrating one example of a jig having the same shape as that of the engaging portion, which is used when forming a model of the dental prosthesis. FIG. 11 is a perspective explanation view illustrating one example of a block for cutting the dental prosthesis, which is cut on the basis of a three-dimensional shape data of the dental prosthesis produced by the present invention.

In the drawings, 1 is a three-dimensional measuring device, which has a measured object mounting tool described below and is used in the method of the present invention. As illustrated in FIG. 1, the three-dimensional measuring device 1 comprises a rotary table 1a, a XY table 1c, and a measuring part id. In this device, the rotary table 1a has an axial center of a rotating shaft, which is a Z axis. The XY table 1c has a placing table 1b for providing a measured object mounting tool 2, which is fixed on the upper part thereof, is movable in the X axial direction and the Y axial direction and is arranged on the rotary table 1a. The measuring part 1d is for measuring the three-dimensional coordinates of the shape of the measured object by one laser sensor 1da, where the measured object is mounted on the measured object mounting tool 2 on the placing table 1b. The laser sensor 1da rotationally moves on one plane containing the Z axis around a desired point on the Z axis, and moves in the Z axial direction.

The three-dimensional measuring device 1 is used for measuring the three-dimensional coordinates of the shape of the measured object mounted on the measured object mounting tool 2 by the measuring part 1d, where this tool is provided at the upper part of the placing table 1b, to thereby produce the three-dimensional shape data of the dental prosthesis for cutting a block B for cutting the dental prosthesis by an automatic cutting device, in order to have the same shape as that of the measured object.

For measuring the three-dimensional coordinates of the shape of the measured object by using the three-dimensional measuring device 1, the following steps are carried out. The steps are, moving the measured object to the X axis direction and Y axis direction by the XY table 1c, where the object is mounted on the measured object mounting tool 2 provided at the upper part of the placing table, rotating the object around the Z axis by the rotary table 1a, where the Z axis is the center axis of the rotary shaft of the rotary table 1a, rotationally moving the one laser sensor 1da itself of the measuring part 1d on one plane containing the Z axis around on the desired point on the Z axis, moving the sensor 1da on the Z axial direction, irradiating the laser light on the surface of the measured object by the one laser sensor 1da, receiving the laser light reflected from the face of the measured object, measuring the three-dimensional coordinates of each point of the surface of the measured object on the basis of a position of the laser sensor 1da, a received light angle of the laser light, a received light amount of the laser light, time from irradiating to receiving the light, or the like, when receiving the laser light by the measuring part 1d, and thereby, obtaining the three-dimensional coordinates of the shape of the measured object on the basis of a plurality of these measuring points.

2 is a measured object mounting tool, which is placed on the upper part of the placing table 1b on the XY table 1c of the three-dimensional measuring device 1. The measured object mounting tool 2 comprises a cylindrical part 2a, a placing part 2b, an inclined part 2c, a pillar part 2d, and a mounting part 2e. In this tool, the placing part 2b is formed so as to position a center axis T of the cylindrical part 2a perpendicular with respect to the upper face of the XY table 1c on the placing table 1b, which is on the XY tables 1c provided on the lower face side of the cylindrical part 2a. The inclined part 2c has a part of the conical shape having the angle of 20 to 70 degrees with respect to the center axis T of the cylindrical part 2a at the edge part between the side face and the upper face of the cylindrical part 2a. The pillar part 2d is perpendicularly erected on the upper face side of the cylindrical part 2a, formed to have a same cross sectional shape as the cross sectional shape of an engaging portion 3a of a model 3 of the dental prosthesis and formed so as to position an extension line of the center axis T of the cylindrical part 2a in the engaging portion 3a. The mounting part 2e is formed on the upper face of the pillar part 2d, and has a shape for engaging with an engaging part 3aa of the engaging portion 3a of the model 3 of the dental prosthesis.

The placing part 2b is provided on the lower face side of the cylindrical part 2a of the measured object mounting tool 2, where the part 2b is formed so as to place the cylindrical part 2a on the placing table 1b on the XY table 1c so as to position the center axis T thereof perpendicular with respect to the upper face of the XY table. As for the placing part 2b, for example, as illustrated in FIG. 2, the placing part 2b is formed to have a plurality of engaging protrusions projected downward on the bottom face side of the cylindrical part 2a, and a plurality of engaging grooves so as to engage the plurality of the engaging protrusions with the upper part of the putting table 1b, where the grooves are not illustrated in the drawings. Then, when the XY table 1c or the rotary table 1a are moved in the state of placing the measured object mounting tool 2 on the placing table 1b, the measured object mounting tool 2 is stably placed, without shifting or rotating with respect to the placing table 1b, so that it is preferable.

As illustrated in FIG. 2, the boundary part between the side face and the upper face of the measured object mounting tool 2 has the inclined part 2c, which is a part of the conical shape having the angle of 20 to 70 degrees with respect to the center axis T of the cylindrical part 2a. This inclined part 2c is used for finding the coordinate on the Z axis of a position of the upper end $L_2$ Of the engaging portion 3a of the model 3 of the dental prosthesis, which is necessary when producing the three-dimensional shape data other than the engaging portion 3a.

More particularly, as illustrated in FIG. 5, the coordinate on the Z axis of a position of the lower end $L_1$ of the inclined part 2c of the measured object mounting tool 2 is detected by the steps of keeping the irradiated laser light from the laser sensor 1da of the measuring part 1d of the three-dimensional measuring device 1 to be in parallel with the upper face of the cylindrical part 2a of the measured object mounting tool 2, moving the laser sensor 1da in the Z axial direction so as to transfer the irradiated part by the laser light from the laser sensor 1da to at least the inclined part 2c from the side face of the cylindrical part 2a of the measured object mounting tool 2, measuring the received light amount of the reflected laser light, and detecting the part where the received light amount is remarkably decreased. Then, as illustrated in FIG. 4, the coordinate on the Z axis of the position of the upper end $L_2$ Of the engaging portion 3a of the model 3 of the dental prosthesis is calculated on the basis of the prememorized distance L on the Z axis between the position of the lower end $L_1$ of the inclined part 2c of the measured object mounting tool 2 and the position of the upper end $L_2$ of the engaging portion 3a of the model 3 of the dental prosthesis, in the state of the model 3 of the dental prosthesis being provided on the measured object mounting tool 2.

That is, the laser light irradiated from the laser sensor 1da of the measuring part 1d of the three-dimensional measuring device 1 has the characteristic that the received light amount is increased most when an incident angle with respect to the face of the measured object is orthogonal, and the laser light is reflected irregularly to thereby decrease when the incident angle becomes nearer to 0 or 180 degrees, so that the received light amount becomes smaller. By using this characteristic, the position of the lower end $L_1$ of the inclined part 2c of the measured object mounting tool 2 can be detected.

The method for detecting the position of the lower end $L_1$ of the inclined part 2c of the measured object mounting tool 2 is explained more concretely. For example, when the surface of the measured object mounting tool 2 is applied with a chro-alumite treatment for increasing a reflection efficiency of the laser light, and the inclined part 2c of the measured object mounting tool 2 is a part of the conical shape having the angle of 45 degrees with respect to the center axis T of the cylindrical part 2a at the boundary part between the side face and the upper face of the cylindrical part 2a, the coordinate on the Z axis of the position of the lower end L1 of the inclined part 2c of the measured object mounting tool 2 can be detected by following steps. The steps are, keeping the irradiated laser light from the laser sensor 1da of the measuring part 1d to be in parallel with the upper face of the cylindrical part 2a of the measured object mounting tool 2, and moving the laser sensor 1da in the Z axial direction by the measuring part 1d so as to transfer the irradiated part by the laser light from the laser sensor 1da to at least the inclined part 2c from the side face of the cylindrical part 2a of the measured object mounting tool 2. At this time, the received light amount is kept about 0.4 at the side face of the cylindrical part 2a of the measured object mounting tool 2, but when the irradiated part by the laser light is transferred from the side face of the cylindrical part 2a of the measured object mounting tool 2 to the lower end of the inclined part 2c, the received light amount is remarkably decreased to 0.2 immediately after the transference. Thus, by defecting the part where the received light amount is remarkably decreased, the coordinate on the Z axis of the position of the lower end L1 of the inclined part 2c of the measured object mounting tool 2 can be detected.

Then, the reason why the angle of a part of the conical shape forming the inclined part 2c with respect to the center axis T of the cylindrical part 2a is within the range of 20 to 70 degrees is as follows. When the angle is more than 70 degrees, there is a problem that the reflected laser light is weak to thereby enter the out of the detection range, since the incident angle of the laser light becomes a too obtuse angle. On the other hand, the angle is less than 20 degrees, since the angle with respect to the side face of the cylindrical part 2a is small, the difference between the received light amounts of the laser lights on the side face and the inclined part 2c and the cylindrical part 2a is remarkably small, so that it is hard to find out the part where the received light amount of the laser light is decreased.

The pillar part 2d is perpendicularly erected on the upper face side of the cylindrical part 2a of the measured object mounting tool 2, where the cross sectional shape thereof is same shape as that of the engaging portion 3a of the model 3 of the dental prosthesis, and the extension line of the center axis T of the cylindrical part 2a is positioned in the engaging portion 3a.

The cross sectional shape of the pillar part 2d has the same shape as that of the engaging portion 3a of the model 3 of the dental prosthesis. The reason of this is as follows. When the cross sectional shape of the pillar part 2d is agreed with the cross sectional shape of an engaging portion K which is preformed at the block B for cutting the dental prosthesis, the produced model 3 of the dental prosthesis has the completely same shape as that of the dental prosthesis produced by cutting the block B, so that the shape of the dental prosthesis to be cut can be accurately recognized. As a result of this, in the state where the model 3 of the dental prosthesis is set at the mounting part 2e formed on the upper face of the pillar part 2d, the side face of the pillar part 2d and the side face of the engaging portion 3a are in parallel with the Z axial direction. When a coating treatment such as the chro-alumite treatment or the like, which is preferably used for easily measuring, is applied on the surface of the model 3 of the dental prosthesis, the coating treatment is generally applied immediately before measuring the model 3 of the dental prosthesis in the state of the model 3 of the dental prosthesis being mounted on the measured object mounting tool 2. Thus, the coating is not stored or solidified between the engaging portion 3a and the upper face of the pillar part 2d, or at the mounting part 2e, or the like. Then, it can be prevented that the model 3 of the dental prosthesis becomes undetachable or that an accurate measurement can not be carried out.

Further, the pillar part 2d is perpendicularly erected on the upper face side of the cylindrical part 2a, so as to position the extension line of the center axis T of the cylindrical part 2a in the engaging portion 3a of the model 3 of the dental prosthesis. Thus, the three-dimensional measuring device 1 generally has the state where the axial center of the rotary shaft of the rotary table 1a, which is the Z axis, is agreed with the center line of the placing table 1b on the XY table 1c, before measuring. Thus, as illustrated in FIG. 3, by only placing the measured object mounting tool 2 on the placing table 1b, the center axis T of the cylindrical part 2a of the measured object mounting tool 2 can be agreed with the Z axis. Thus, the three-dimensional coordinates can be smoothly measured by the laser sensor 1da of the measuring part 1d. Further, when three-dimensional coordinates of the model 3 of the dental prosthesis is measured while rotating the rotary table 1a around the Z axis, the three-dimensional coordinates of the model 3 of the dental prosthesis on the basis of the Z axis can be easily obtained.

At this time, when the axial center of the rotary shaft of the rotary table 1a, which is the Z axis of the three-dimensional measuring device 1, is not agreed with the center line of the placing table 1b on the XY table 1c by the various factors before measuring, the both axes can be easily adjusted by the steps of placing the measured object mounting tool 2 on the placing table 1b, and moving the XY tables 1c in the X and/or Y axial directions so as to agree the center axis T of the cylindrical part 2a of the measured object mounting tool 2 with the Z axis, as illustrated in FIG. 3. In this case, the various factors are, for example, a case that the XY table 1c is not accurately returned to the initial position, or a case that the XY table 1c cannot be accurately returned to the initial position since the moving accuracy of the driving means for transferring in the X and/or Y axial directions is deteriorated by secular change or the like.

Further, since the pillar part 2d is perpendicularly erected on the upper face side of the cylindrical part 2a, and the extension line of the center axis T of the cylindrical part 2a is positioned in the engaging portion 3a, the center axis T of the cylindrical part 2a of the measured object mounting tool 2 can be agreed with the Z axis. Thus, only by moving the laser sensor 1da in the Z axial direction by the measuring part 1d, the irradiated part by the laser light from the laser sensor 1da can be easily transferred to the upper position from the side face of the cylindrical part 2a of the measured object mounting tool 2, while keeping the irradiated laser light from the laser sensor 1da in parallel with the upper face of the cylindrical part 2a of the measured object mounting tool 2. Further, the coordinate on the Z axis of the position of the lower end $L_1$ of the inclined part 2c of the measured object mounting tool 2 can be detected on the basis of the Z axis. Further, the coordinate on the Z axis of the position of the upper end $L_2$ of the engaging portion 3a of the model 3 of the dental prosthesis can be calculated, on the basis of the prememorized distance L on the Z axis between the position of the lower end $L_1$ of the inclined part 2c of the measured object mounting tool 2 and the position of the upper end $L_2$ of the engaging portion 3a of the model 3 of the dental prosthesis in the state of the model 3 of the dental prosthesis being mounted on the measured object mounting tool 2.

The upper face of the pillar part 2d of the measured object mounting tool 2 has the mounting part 2e having the shape for engaging with the engaging part 3aa of the engaging portion 3a of the model 3 of the dental prosthesis. As for the mounting part 2e, for example, when the engaging part 3aa of the engaging portion 3a of the model 3 of the dental prosthesis is a recessed engaging hole having the cross sectional shape of regular hexagon as illustrated in FIGS. 6 and 7, the mounting part 2e is formed to have a projected pillar body having the cross sectional shape of regular hexagon as illustrated in FIG. 2. Further, for example, when the engaging part 3aa of the engaging portion 3a of the model 3 of the dental prosthesis has a cylindrical shape projected part on the jawbone side and a plurality of semicircular shape projected parts provided on the circumference of the cylindrical shape projected part at equal intervals, the mounting part 2e is recessed to be formed like the engaging holes having the cross sectional shapes for engaging with such the engaging part 3aa, though not illustrated in the drawings.

3 is a model of the dental prosthesis, which is the measured object, with the engaging portion 3a having the projected and/or recessed engaging part 3aa being projected on the jawbone side and having the cross sectional shape other than the shape of the rotary body. The model 3 of the dental prosthesis is formed with a material such as wax, synthetic resin, gypsum or the like, by a dental technician.

As for the engaging part 3aa formed at the engaging portion 3a projected on the jawbone side of the model 3 of the dental prosthesis, it is not limited if the cross sectional shape is a shape other than the rotary body, that is, the cross sectional shape is a projected and/or recessed shape having the shape other than a right circle. However, when a preferable cross sectional shape of the engaging part 3aa is such shape that the completely same external shape appears repeatedly for every rotation of 360 degrees/n (n is a positive integer of 2 or more) and the graphic formed with n-time rotations is not circular, for example, the cross sectional shape of the engaging part 3aa of the engaging portion 3a of the model 3 of the dental prosthesis has a shape, such as the recessed engaging hole having the cross sectional shape of regular hexagon as illustrated in FIGS. 6 and 7, or a rotationally symmetric shape, such as a shape formed with the cylindrical shape projected on the jawbone side and the plurality of the semicircular projected parts provided on the circumference face of the cylindrical shape at equal intervals, as illustrated in FIGS. 8 and 9. When the engaging part has such the shape, the model 3 of the dental prosthesis can be easily mounted on the measured object mounting tool 2, since there are a plurality of mounting directions. Further, the engaging portion of the dental prosthesis has a shape not having a part where the remarkably strong force is applied around its center axis, to thereby produce the excellent dental prosthesis, so that it is preferable.

As an example of the model 3 of the dental prosthesis, there is an abutment having a shape, in which a portion contacting with the gingival and a portion fixed with the artificial tooth are designed in accordance with the shape of the gingival or the adjacent tooth and also an engaging portion for engaging with the implant fixture embedded into the jawbone is provided, as illustrated in FIGS. 6 and 7. In addition, there is a model 3 of the dental prosthesis having the shape where the artificial tooth is integrated with the engaging portion, and provided and fixed directly or through the present abutment at a part of the oral cavity side of the implant fixture which is embedded into the jawbone, as illustrated in FIGS. 8 and 9.

As a method for forming the model 3 of the dental prosthesis, the following methods can be used. The method comprisies building wax or the like directly on a gypsum model mold having a shape of an adjacent tooth, a lost tooth, an abutment tooth or the like, which is produced beforehand, to thereby make the model 3 of the dental prosthesis, or directly building the wax or the like on the mounting part 2e of the pillar part 3d of the measured object mounting tool 2, to thereby make the model 3 of the dental prosthesis. However, a preferable method comprises preparing a jig and directly building the wax or the like on the jig, where the jig has the engaging portion having the same shape as that of the engaging portion 3a of the model 3 of the dental prosthesis, and has a shape capable of forming the part other than the engaging portion on the upper side thereof, as illustrated in FIG. 10. This method is preferable since the shape of the engaging portion of the dental prosthesis can be accurately reproduced. Further, since the model 3 of the dental prosthesis can be formed with complete understanding of the shape of the engaging portion, it is possible to increase the feeling of use, the aesthetic appreciation or the like of the finally produced dental prosthesis, so that it is preferable.

Then, each step of one aspect of the production method of the three-dimensional shape data of the dental prosthesis by using the three-dimensional measuring device 1 structured as above and the measured object mounting tool 2 in accordance with the present invention is described in order, where the data is for cutting the block B for cutting the dental prosthesis as illustrated in FIG. 11 by the automatic cutting machine to have the same shape as that of the model 3 of the dental prosthesis, which is the measured object.

First, the model preparing steps is carried out for preparing the model 3 of the dental prosthesis, with the engaging portion 3a having the projected and/or recessed engaging part 3aa being projected on the jawbone side and having the cross sectional shape other than that of the rotary body. The model preparing step is carried out before measuring, by preparing the model 3 of the dental prosthesis preformed using the material such as the wax, the synthetic resin, the gypsum or the like, by the dental technician or the like.

Then, the model providing step is carried out by preparing the measured object mounting tool 2 according to the present invention, and engaging the engaging part 3aa of the engaging portion 3a of the model 3 of the dental prosthesis with the mounting part 2e of the measured object mounting tool 2, where the model 3 of the dental prosthesis is prepared by the model preparing step.

Then, the mounting tool placing step is carried out for placing the measured object mounting tool 2 having the model 3 of the dental prosthesis on the placing table, where the model 3 of the dental prosthesis is provided by the model providing step.

At this time, the pillar part 2d of the measured object mounting tool 2 is perpendicularly erected on the upper face side of the cylindrical part 2a and the extension line of the center axis T of the cylindrical part 2a is positioned in the engaging portion 3a of the model 3 of the dental prosthesis. The three-dimensional measuring device 1 generally has the constitution, in the stage before measuring, that the axial center of the rotary shaft 1a, which is the Z axis, is agreed with the center line of the placing table 1b on the XY tables 1c. Thus, only by placing the measured object mounting tool 2 on the placing table 1b, the center axis T of the cylindrical part 2a of the measured object mounting tool 2 can be agreed with the Z axis, as illustrated in FIG. 3. Therefore, the three-dimensional coordinates can be smoothly measured by the laser sensor 1da of the measuring part 1d. Further, when three-dimensional coordinates of the model 3 of the dental prosthesis is measured while rotating the rotary table 1a around the Z axis, it is possible to easily obtain the three-dimensional coordinates of the model 3 of the dental prosthesis on the basis of the Z axis.

At this time, when the axial center of the rotary shaft of the rotary table 1a, which is the Z axis of the three-dimensional measuring device 1, is not agreed with the center line of the placing table 1b on the XY table 1c in the stage before measuring by the various factors, the both axes adjusting step is further carried out, so that the XY table is moved in the X axial direction and/or the Y axis direction to agree the center axis of the cylindrical part 2a of the measured object mounting tool 2 with the Z axis, after carrying out the mounting tool placing step. The various factors are, for example, a case that the XY table 1c is not accurately returned to the initial position, or a case that the XY table 1c can not be accurately returned to the initial position since the moving accuracy of the driving means for transferring in the X and/or Y axial directions is deteriorated by secular change or the like.

For carrying out the both axes adjusting step, for example, the moving distance of the XY table 1c in the X and Y axial directions are inputted so as to return those to the initial positions, where the axial center of the rotary shaft 1a comprising the Z axis is agreed with the center line of the placing table 1b on the XY table 1c. However, when the both axes adjusting step comprises a mounting tool coordinate measuring step, a correction value calculating step and a position correcting step, it is preferable to be able to agree the both axes automatically. The mounting tool coordinate measuring step is for measuring a two-dimensional XY coordinates of a even number plurality of points positioned at the periphery face of the cylindrical part 2a of the measured object putting tool 2 by the measuring part 1d of the three-dimensional measuring device 1. The correction value calculating step comprises steps of calculating sum total of the values of the X axial coordinate and the Y axial coordinate of each point measured, dividing each sum total by the numbers of the measured points to thereby obtain the XY coordinates of the center axis T of the measured object mounting tool 2, where the Z axis is an original point, calculating the difference of the coordinates between the two-dimensional XY coordinate of the center axis T and the original point, and thereby obtaining the correction value of the center axis T of the measured object mounting tool 2. The position correcting steps comprises steps of transferring the XY table 1c in the X and/or the Y axial directions on the basis of the obtained correction value, and thereby adjusting the center axis T of the cylindrical part 2a of the measured object mounting tool 2 with the Z axis. Then, the both axes can be accurately agreed automatically, in the case that the transferring accuracy of the driving means for transferring the XY table 1c in the X axial and/or the Y axial directions is deteriorated by the secular change, and the center axis T of the cylindrical part 2a of the measured object mounting tool 2 and the Z axis cannot be easily agreed, even when inputting to the driving means in order to return the XY table 1c to the initial position where the axial center of the rotary shaft of the rotary table 1a being the Z axis is agreed with the center line of the placing table 1b on the XY table 1c. Thus, it is preferable. Further, even when the XY table 1c is not returned to the initial position, the both axes can be automatically agreed, without inputting to each driving means of the XY table 1c for transferring the XY table 1c to the initial positions. Thus, it is preferable.

Further, in the both axes adjusting step, when the mounting tool coordinate measuring step, the correction value calculating step, and the position correcting step are repeated until the correction value calculated by the correction value calculating step becomes a minimum unit or less by which the XY tables 1c can be moved, the center axis T of the cylindrical part 2a of the measured object mounting tool 2 can be more accurately agreed with the Z axis, so that it is preferable.

Then, a model mounted tool measuring step is carried out by steps of rotating the rotary table 1a around the Z axis as the axial center, keeping the laser light from the laser sensor 1da of the measuring part to be in parallel with the upper face of the cylindrical part 2a of the measured object mounting tool 2, moving the laser sensor 1da by the measuring part 1d in the Z axial direction so as to transfer the laser light irradiated portion from the laser sensor 1da to the position of the height before reaching to the top of the pillar part 2d of the measured object mounting tool 2 from the side face of the cylindrical part 2a of the measured object mounting tool 2 through the inclined part 2c of the measured object mounting tool 2, and rotationally moving the laser sensor 1da for measuring the received light amount of the laser light from the cylindrical part 2a and the pillar part 2d of the measured object mounting tool 2 and the model 3 of the dental prosthesis, and the three-dimensional coordinate of these shapes.

At this time, as illustrated in FIG. 5, the laser sensor 1da moves to the position of the height before reaching to the top part of the pillar part 2d, while keeping the irradiated laser light in parallel with the upper face of the cylindrical part 2a of the measured object mounting tool 2. Then, the laser sensor 1da rotationally moves on one plane containing the Z axis around the desired point on the Z axis from the position of the height before reaching to the top part of the pillar part 2d, along a circular arc orbit. Then, the received light amount of the laser light in a portion from the cylindrical part 2a of the measured object mounting tool 2 to the model 3 of the dental prosthesis is measured gradually, and the three-dimensional coordinates of the shape, where the part of the upper side from the cylindrical part 2a of the measured object mounting tool 2 is integrated with the model 3 of the dental prosthesis, is measured.

Finally, a three-dimensional coordinate extracting step is carried out by steps of detecting the position where the received light amount of the laser light is remarkably decreased when transferring from the side face of the cylindrical part 2a of the measured object mounting tool 2 to the inclined part 2c, detecting the coordinate on the Z axis of the position of the lower end $L_1$ of the inclined part 2c of the measured object mounting tool 2, calculating the coordinate on the Z axis of the position of the upper end $L_2$ of the engaging portion 3a of the model 3 of the dental prosthesis on the basis of the prememorized distance L on the Z axis between the position of the lower end $L_1$ of the inclined part 2c of the measured object mounting tool 2 and the upper end $L_2$ of the engaging portion 3a of the model 3 of the dental prosthesis, where the model 3 of the dental prosthesis is provided on the measured object mounting tool 2, and extracting only the three-dimensional coordinates of the shape other than the engaging portion 3a of the model 3 of the dental prosthesis, where the shape is positioned on the upper side from the coordinate calculated from the measured three-dimensional coordinate.

At this time, for example, in the case that the surface of the measured object mounting tool 2 is applied with the chroalumite treatment, and the inclined part 2c of the measured object mounting tool 2 has a part of the conical shape having the angle of 45 degrees with respect to the center axis T of the cylindrical part 2a at the boundary part between the side face and the upper face of the cylindrical part 2a, the received light amount at the side face of the cylindrical part 2a is kept about 0.4. However, when the irradiated part by the laser light is transferred from the side face of the cylindrical part 2a of the measured object mounting tool 2 to the lower end of the inclined part 2c, the received light amount is remarkably decreased to 0.2 immediately after transferring. Thus, by detecting the part where the received light amount is remarkably decreased, the coordinate on the Z axis of the position $L_1$ of the lower end of the inclined part 2c of the measured object mounting tool 2 can be detected.

Further, the distance L is used when calculating the coordinate on the Z axis of the position of the upper end $L_2$ of the engaging portion 3a of the model 3 of the dental prosthesis. The distance L is a distance on the Z axis between the position of the lower end $L_1$ of the inclined part 2c of the measured object mounting tool 2 and the position of the upper end $L_2$ of the engaging portion 3a of the model 3 of the dental prosthesis in the state of the model 3 of the dental prosthesis being mounted on the measured object mounting tool 2. In order to decide the L, the distance in the Z axial direction, that is, the distance in the direction of the center axis T of the cylindrical part 2a of the measured object mounting tool 2 of the both positions is measured beforehand in the state of providing the model 3 of the dental prosthesis on the measured object mounting tool 2 as illustrated in FIG. 4. The measured value is used as the distance L and prememorized in the measuring part 1d or the like of the three-dimensional measuring device 1.

The present invention has the constitution, where the coordinate on the Z axis of the position of the upper end $L_2$ of the engaging portion 3a of the model 3 of the dental prosthesis is calculated on the basis of the prememorized distance L, from the detected coordinate of the position of the lower end $L_1$ of the inclined part 2c of the measured object mounting tool 2. Thus, the accurate coordinate on the Z axis of the position of the upper end $L_2$ of the engaging portion 3a of the model 3 of the dental prosthesis can be obtained. Further, the three-dimensional coordinate, which is positioned on the upper side of the coordinate on the Z axis of the position of the upper end $L_2$ of the engaging portion 3a of the model 3 of the dental prosthesis, is extracted from the three-dimensional coordinate of the shape measured by the model mounted tool measuring step, where the upper side portion from the cylindrical part 2a of the measured object mounting tool 2 and the model 3 of the dental prosthesis are integrated. Then, the accurate three-dimensional shape data having the shape other than the engaging portion 3a of the model 3 of the dental prosthesis can be produced only by this extracting.

Next, as for another aspects of the production method of the three-dimensional shape data of the dental prosthesis for cutting the block B for cutting the dental prosthesis by the automatic cutting machine to have the same shape as that of the model 3 of the dental prosthesis, which is the measured object by using the three-dimensional measuring device 1 and the measured object mounting tool 2 of the present invention, each step is explained in order. However, since the constitutions from the model preparing step to the mounting tool placing step and the both axes adjusting step in the aspect where the both axes adjusting step is carried out further after the mounting tool placing step are substantially the same constitutions as those of the above aspects, the explanations are omitted.

First, in case of the aspect where the steps from the model preparing step to the mounting tool placing step are carried out in order and then the both axes adjusting step is further carried out, the measuring initial position moving step is carried out, after the both axes adjusting step, by steps of moving the laser sensor 1da in the Z axis direction by the measuring part 1d so as to transfer the irradiated portion by laser light from the laser sensor 1da from the side face of the cylindrical part 2a of the measured object mounting tool 2 to the inclined face 2c of the measured object mounting tool 2, while keeping the laser light from the laser sensor 1da of the measuring part 1d to be irradiated in parallel to the upper face of the cylindrical part 2a of the measured object mounting tool 2, detecting the point where the received light amount of the laser light is extremely decreased, to thereby detect the coordinate on the Z axis of the lower end $L_1$ of the inclined part 2c of the measured object mounting tool 2, calculating the coordinate on the Z axis of the position of the upper part $L_2$ of the engaging portion 3c of the model 3 of the dental prosthesis, on the basis of the prememorized distance L on the Z axis between the positions of the lower end $L_1$ of the inclined part 2c of the measured object mounting tool 2 and the upper end $L_2$ of the engaging portion 3c of the model 3 of the dental prosthesis, where the model 3 of the dental prosthesis is provided on the measured object mounting tool 2, transferring quickly the laser sensor 1da by the measuring part 1d in the Z axis direction to the calculated position $L_2$ of the coordinate on the Z axis. In addition, when the measuring initial position moving step is carried out, this step may be carried out in the state where the rotation of the rotary table 1a is stopped. However, when the step is carried out while rotating the rotary table 1a around the Z axis, the irradiated part by the laser light from the laser sensor 1da covers the whole of the surrounding of the measured object mounting tool 2. Thus, the accuracy when detecting the position, where the received light amount of the laser light is remarkably decreased, is enhanced, so that it is preferable.

At this time, as illustrated in FIG. 5, when the laser sensor 1da is moved in the Z axial direction while keeping the irradiated laser light from the laser sensor 1da to be in parallel with the upper face of the cylindrical part 2a of the measured object mounting tool 2, to thereby detect the coordinate on the Z axis of the position of the lower end $L_1$ of the inclined part 2c of the measured object mounting tool 2, that is, when the position where the received light amount of the laser light is remarkably decreased can be detected, the measuring by the laser light is once stopped. Then, the coordinate on the Z axis of the position of the upper end $L_2$ of the engaging portion 3a of the model 3 of the dental prosthesis is calculated the calculated coordinate on the Z axis of the position of the lower end $L_1$ of the inclined part 2c of the measured object mounting tool 2 the basis of the prememorized distance L on the Z axis between the position of the lower end $L_1$ of the inclined part 2c of the measured object mounting tool 2 and the position of the upper end $L_2$ of the engaging portion 3a of the model 3 of the dental prosthesis, where the model of the dental prosthesis 3 is provided on the measured object mounting tool 2. Then, the laser sensor 1da is moved in the Z axial direction quickly to the position of the upper end L2 of the engaging portion 3a of the model 3 of the dental prosthesis, that is, to the initial position where the shape other than the engaging portion 3a of the model 3 of the dental prosthesis can be immediately measured.

Finally, the model mounted tool measuring step is carried out. This step is for measuring the three-dimensional coordinate of the shape other than the engaging portion 3a of the model 3 of the dental prosthesis by rotationally moving the laser sensor 1da, while rotating the rotary table 1a around the Z axis.

At this time, the laser sensor 1da has been moved to the initial position, where only the three-dimensional coordinates of the shape other than the engaging portion 3a of the model 3 of the dental prosthesis can be measured, by the measuring initial position moving step. Thus, by rotationally moving the laser sensor 1da from the initial position while rotating the rotary table 1a around the Z axis, the accurate three-dimensional shape data of the shape other than the engaging portion 3a of the model 3 of the dental prosthesis can be easily produced.

Then, the method for cutting the block B for cutting the dental prosthesis by the automatic cutting machine is explained, where the block B has been cut by using the three-dimensional shape data of the dental prosthesis produced by the method of the present invention, and an engaging portion K having the approximately same shape as that of the engaging portion 3a of the model 3 of the dental prosthesis is preformed in the block B.

First, the block B for cutting the dental prosthesis is prepared beforehand, where the engaging portion K has the approximately same shape as that of the engaging portion 3a of the model 3 of the dental prosthesis. The preferably used block B, for example, has a shape having a preformed engaging portion K as shown in FIG. 11 and a material thereof is a titanium alloy, a ceramic before or after baking, a composite resin or the like.

After finishing such the preparation, the operation for providing the block B in the automatic cutting machine is carried out at first. At this time, the block B is provided in the automatic cutting machine so as to direct the block B in the predetermined direction.

Then, the three-dimensional shape data of the dental prosthesis, which is produced by the method of the present invention, is inputted to the automatic cutting machine, and the operation for cutting the block B is carried out on the basis of the inputted three-dimensional shape data of the dental prosthesis.

At this time, the three-dimensional shape data of the dental prosthesis inputted to the automatic cutting machine is the accurate data of the shape other than the engaging portion 3a of the model 3 of the dental prosthesis produced by the method of the present invention, that is, the three-dimensional shape of the shape data of the part positioned on the upper side of the upper end $L_2$ of the engaging portion 3a of the model 3 of the dental prosthesis. Thus, when the cutting is started from the upper end of the engaging portion K of the block B, where the engaging portion K having the approximately same shape as that of the engaging portion 3a is preformed, on the basis of the position of the upper end $L_2$ of the engaging portion 3a of the model 3 of the dental prosthesis in the inputted three-dimensional shape data, it is possible to obtain the dental prosthesis having the accurately same shape as that of the model 3 of the dental prosthesis and especially the accurately same shape nears the upper side of the engaging portion 3a as that of the model 3 of the dental prosthesis.

What is claimed is:

1. A method of producing three-dimensional shape data of a dental prosthesis for cutting a block to form the dental prosthesis by an automatic cutting machine to have a same shape as that of a measured object, by using the three-dimensional measuring device comprising:

a rotary table having a rotating shaft, and an axis of the rotating shaft is a first axis, a table, including a placing table to fixedly provide a measured object mounting tool on an upper part thereof, wherein the table is movable in directions along a second axis and a third axis and is arranged on the rotary table, and a measuring part to measure three-dimensional coordinates of a shape of a measured object mounted on the measured object mounting tool on the placing table by one laser sensor rotationally moving in a plane containing the first axis around a desired point on the first axis and moving in a direction parallel to the first axis, wherein said method of producing comprises:

preparing a model of the dental prosthesis, which is the measured object, wherein said model of the dental prosthesis has an engaging portion projected on a jawbone side which has a projected and/or recessed engaging part having a cross sectional shape other than that of a rotary body;

preparing the measured object mounting tool;

engaging the engaging part of the engaging portion of the model of the dental prosthesis with a mounting part of the measured object mounting tool;

placing the measured object mounting tool with the model of the dental prosthesis on the placing table;

rotating the rotary table around the first axis to keep laser light irradiated from the laser sensor of the measuring part in parallel with an upper face of a cylindrical part of the measured object mounting tool;

moving the laser sensor in the direction parallel to the first axis via the measuring part so as to transfer a portion irradiated by the laser light to a position of a height before reaching a top of a pillar part from a side face of the cylindrical part of the measured object mounting tool passing through an inclined part of the measured object mounting tool and then rotationally moving the laser sensor to thereby measure received light amounts of the laser light from the cylindrical part and the pillar part of the measured object mounting tool and the model of the dental prosthesis, and the three-dimensional coordinates of shapes thereof;

detecting a position where the received light amount of the laser light is remarkably decreased when transferring from the side face of the cylindrical part of said measured object mounting tool to the inclined part;

detecting a coordinate on the first axis of a position of a lower end of the inclined part of the measured object mounting tool;

calculating a coordinate on the first axis of a position of an upper end of the engaging portion of the model of the dental prosthesis based on a prememorized distance along the first axis between the position of the lower end of the inclined part of the measured object mounting tool and the position of the upper end of the engaging portion of the model of the dental prosthesis, wherein the model of the dental prosthesis is provided on the measured object mounting tool; and extracting only the three-dimensional coordinates of the shape other than the engaging portion of the model of the dental prosthesis positioned on an upper side of the coordinate calculated from the measured three-dimensional coordinates, so that said three-dimensional shape data of the dental prosthesis for cutting the block to form the dental prosthesis by the automatic cutting machine is produced by carrying out said method in order, wherein an engaging portion of the dental prosthesis has approximately a same shape as the engaging portion of the model of the dental prosthesis.

2. A method of producing three-dimensional shape data of a dental prosthesis for cutting a block to form the dental prosthesis by an automatic cutting machine to have a same shape as that of a measured object, by using the three-dimensional measuring device comprising;
- a rotary table having a rotating shaft, and a axis of the rotating shaft is a first axis,
- a table including a placing table to fixedly provide a measured object mounting tool on an upper part thereof, wherein the table is movable in directions along a second axis and a third axis and is arranged on the rotary table, and
- a measuring part to measure three-dimensional coordinates of a shape of a measured object mounted on the measured object mounting tool on the placing table by one laser sensor rotationally moving in a plane containing the first axis around a desired point on the first axis and moving in a direction parallel to the first axis, wherein said method of producing comprises:
- preparing a model of the dental prosthesis, which is the measured object, wherein said model of the dental prosthesis has an engaging portion projected on a jawbone side which has a projected and/or recessed engaging part having a cross sectional shape other than that of a rotary body;
- preparing the measured object mounting tool;
- engaging the engaging part of the engaging portion of the model of the dental prosthesis with a mounting part of the measured object mounting tool;
- placing the measured object mounting tool with the model of the dental prosthesis on the placing table;
- keeping laser light irradiated from the laser sensor of the measuring part in parallel with an upper face of a cylindrical part of the measured object mounting tool;
- moving the laser sensor in the direction parallel to the first axis via the measuring part so as to transfer a portion irradiated by the laser light from a side face of the cylindrical part of the measured object mounting tool to an inclined part of the measured object mounting tool;
- detecting a position where the received light amount of the laser light is remarkably decreased,
- detecting a coordinate on the first axis of a position of a lower end of the inclined part of the measured object mounting tool;
- calculating a coordinate on the first axis of a position of an upper end of the engaging portion of the model of the dental prosthesis based on a prememorized distance along the first axis between the position of the lower end of the inclined part of the measured object mounting tool and the position of the upper end of the engaging portion of the model of the dental prosthesis, wherein the model of the dental prosthesis is provided on the measured object mounting tool; and
- moving the laser sensor, in the direction parallel to the first axis to the calculated coordinate, by the measuring part, and
- rotating and moving the laser sensor, while rotating the rotary table around the axis, and measuring the three-dimensional coordinates of the shape of the model of the dental prosthesis other than the engaging portion,
- so that said three-dimensional shape data of the dental prosthesis for cutting the block to form the dental prosthesis by the automatic cutting machine is produced by carrying out said method in order, wherein an engaging portion of the dental prosthesis has approximately a same shape as the engaging portion of the model of the dental prosthesis.

3. The method of producing a three-dimensional shape data of the dental prosthesis as claimed in claim 1, further comprising:
- moving the table in the directions along the second axis and the third axis so as to align a center axis of the cylindrical part of the measured object mounting tool with the first axis,
- wherein the moving the table is performed after the placing the measured object mounting tool.

4. The method of producing a three-dimensional shape data of the dental prosthesis as claimed in claim 2, further comprising:
- moving the table in the directions along the second axis and the third axis so as to align a center axis of the cylindrical part of the measured object mounting tool with the first axis,
- wherein the moving the table is performed after the placing the measured object mounting tool.

* * * * *